United States Patent

Sitzmann

[11] Patent Number: 5,194,659
[45] Date of Patent: Mar. 16, 1993

[54] HIGH MELTING AMINO AROMATIC NITRATE ESTERS

[75] Inventor: Michael E. Sitzmann, Adelphi, Md.

[73] Assignee: The United States of America as represented by the Secretary of the Navy, Washington, D.C.

[21] Appl. No.: 901,618

[22] Filed: Jun. 15, 1992

[51] Int. Cl.⁵ ............................................. C07C 203/10
[52] U.S. Cl. ..................................... 558/482; 149/105; 568/932
[58] Field of Search ....................... 558/482; 149/105; 568/932

[56] References Cited

U.S. PATENT DOCUMENTS 3,544,630 12/1970 Frankel ........................... 149/105 X
5,034,073 7/1991 Barry et al. ..................... 149/105 X
5,081,255 1/1992 Sitzmann ........................... 548/145

Primary Examiner—Richard D. Lovering
Assistant Examiner—C. Samala
Attorney, Agent, or Firm—Kenneth E. Walden; Roger D. Johnson

[57] ABSTRACT

A nitrate ester which is 1,3-diamino-5-(hydroxyethylaminonitrate)-2,4,6-trinitrobenzene or 3-amino-3'-(hydroxyethylaminonitrate)-2,2',4,4',6,6'-hexanitrobiphenyl.

2 Claims, No Drawings

HIGH MELTING AMINO AROMATIC NITRATE ESTERS

BACKGROUND OF THE INVENTION

This invention relates to organic nitrate esters and more particularly to aromatic nitrate esters which are useful as explosives.

The availability of high-melting nitrate esters is very limited. Pentaerythritol tetranitrate (PETN) is the highest melting of commonly available nitrate esters, but its melting point (140° C.) precludes its use at temperatures in the vicinity of 150° C. and above [missile systems often require explosives that can withstand short-term (30 minutes) exposure to temperatures in the vicinity of 150° C. and above due to aerodynamic heating]. A higher melting (mp 158°-160° C.) nitrate ester, 2,4,6-trinitro-1,3,5-tris(2-hydroxyethylnitramino)benzenetrinitrate, has been reported but its availability is limited by procedures that provide low to moderate yields (approximately 50%). Thus, it would be advantageous to have available a method that provides high yields of high-melting nitrate esters to allow a wide range of melting points and sensitivities as well as short-term stability at 150° C.

U.S. Pat. No. 5,081,255, titled, "High melting Aromatic Nitrate Esters," which issued Jan. 14, 1992 to Michael E. Sitzmann discloses 2,4,6-trinitro-1-(2-hydroxyethylamino)-3-(2-hydroxyethylnitramino)benzenedinitrate; 2,2',4,4'6,6'-hexanitro-3-(2-hydroxyethylnitramino)stilbenenitrate; 1,3,5-tris(hydroxyethylaminonitrate)-2,4,6-trinitrobenzene; 2,5-bis[3-(hydroxyethylaminonitrate)-2,4,6-trinitrophenyl]-1,3,4-oxadiazole; and 2,5-bis[3-hydroxyethylaminonitrate)-5-(hydroxyethylnitraminonitrate)-2,4,6-trinitrophenyl]-1,3,4-oxadiazole which are energetic explosive compounds having suitably high melting or decomposition points. Nevertheless, it would be desirable to provide explosives which are even more resistant to high temperatures.

SUMMARY OF THE INVENTION

Accordingly an object of this invention is to provide novel, high energy nitrate esters with high melting (or decomposition) points.

Another object of this invention is to provide nitrate esters that have short term stability even at temperatures above 150° C.

A further object of this invention is to provide temperature resistant nitrate esters which are useful as initiation train explosives and/or as booster explosives.

These and other objects of this invention are achieved by providing:

A nitrate ester which is 1,3-diamino-5-(hydroxyethylaminonitrate) -2,4,6-trinitrobenzene or 3-amino-3'-(hydroxyethylaminonitrate)-2,2',4,4',6,6'-hexanitrobiphenyl.

DETAILED DESCRIPTION OF THE PREFERRED EMBODIMENT

The explosive compounds of this invention are the following high-melting amino polynitroaromatic nitrate esters: 1,3-diamino-5-(hydroxyethylaminonitrate)-2,4,6-trinitrobenzene(215° C. dec.),

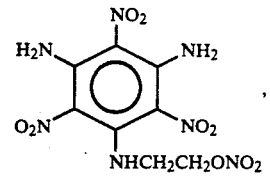

and 3-amino-3'-(hydroxyethylaminonitrate)-2,2',4,4',6,6'-hexanitrobiphenyl (182° C. dec.),

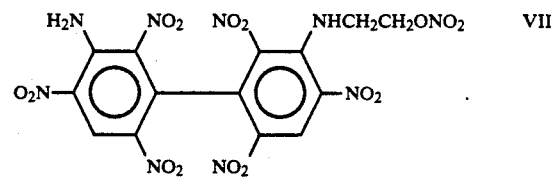

U.S. Pat. No. 5,081,255, cited above, discloses 1,3,5-tris(hydroxyethylaminonitrate)-2,4,6-trinitrobenzene,

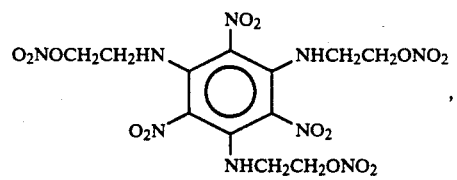

with a melting point of 186° C. Replacement of one of the —NHCH2CH2ONO2 groups with an —NH2 group produces 1-amino-3,5-bis(hydroxyethylaminonitrate)-2,4,6-trinitrobenzene,

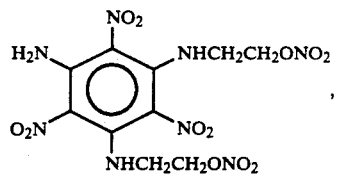

with a melting point of only 110°-112° C., making this compound unsuitable for high temperature applications. However, it has been discovered that when two —NHCH2CH2ONO2 groups are replaced with two —NH2 groups the compound 1,3-diamino-5-(hydroxyethylaminonitrate)-2,4,6-trinitrobenzene (I) does not melt until 215° C. where it decomposes. As a result, 1,3-diamino-5-(hydroxyethylaminonitrate)-2,4,6-trinitrobenzene is suitable for high temperature applications such as in aerodynamically heated missile warheads.

The nitrate ester 3,3'-bis(hydroxyethylaminonitrate)-2,2',4,4',6,6'-hexanitrobiphenyl,

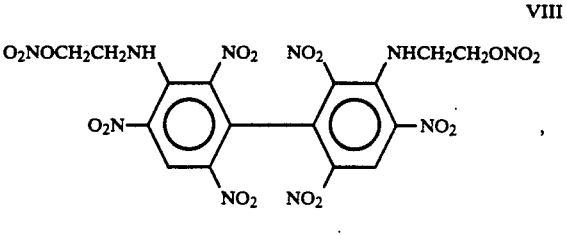

has a melting point of 138°–140° C., and is therefore not suitable for use at the temperature of 150° C. and above which occur in aerodynamically heated missile war heads. However, replacing one —NHCH₂CH₂ONO₂ group with a —NH₂ group produces 3-amino-3'-hydroxyethylaminonitrate)-2,2',4,4',6,6'-hexanitrobiphenyl (VII),

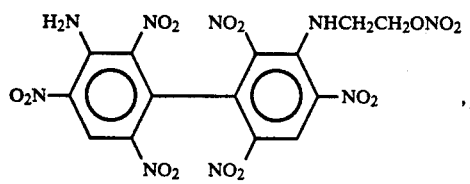

which has a melting (decomposition) point of 182° C. and which is therefore suitable for use in the missile warheads.

The substitution of —NH₂ groups for —NHCH₂CH₂ONO₂ may also lower the sensitivity of the explosive compound. For example, the impact sensitivity of crystallized 1,3-diamino-5-(hydroxyethylaminonitrate)-2,4,6-trinitrobenzene was found to be 50 cm (RDX=19 cm). A similarly crystallized sample 1,3,5-tris(hydroxyethylaminonitrate)-2,4,6-trinitrobenzene was found to have an impact sensitivity of 43 cm but a fine particle sized sample was found to have an impact sensitivity of 23 cm.

The reaction sequence for preparing 1,3-diamino-5-(hydroxyethylaminonitrate)-2,4,6-trinitrobenzene can be summarized as follows:

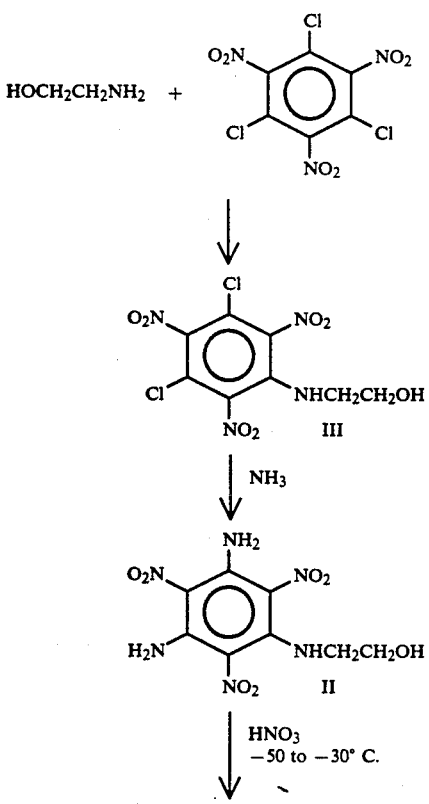

-continued

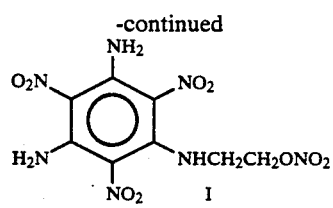

First, one mole of ethanolamine is reacted with each mole of 1,3,5-trichloro-2,4-6-trinitrobenzene under the conditions given in example 1 to give 1,3-dichloro-5-(2-hydroxyethylamino)-2,4,6-trinitrobenzene (compound III). Compound III is then reacted with ammonia under the conditions given in example 2 to produce 1,3-diamino-5-(2-hydroxyethylamino)-2,4,6-trinitrobenzene (compound II). Compound II is then nitrated under the conditions given in example 3 to give the product 1,3-diamino-5-(hydroxyethylaminonitrate)-2,4,6-trinitrobenzene (I).

The reaction sequence for preparing 3-amino-3'-(hydroxyethylaminonitrate)-2,2',4,4',6,6'-hexanitrobiphenyl (VII) can be summarized as follows:

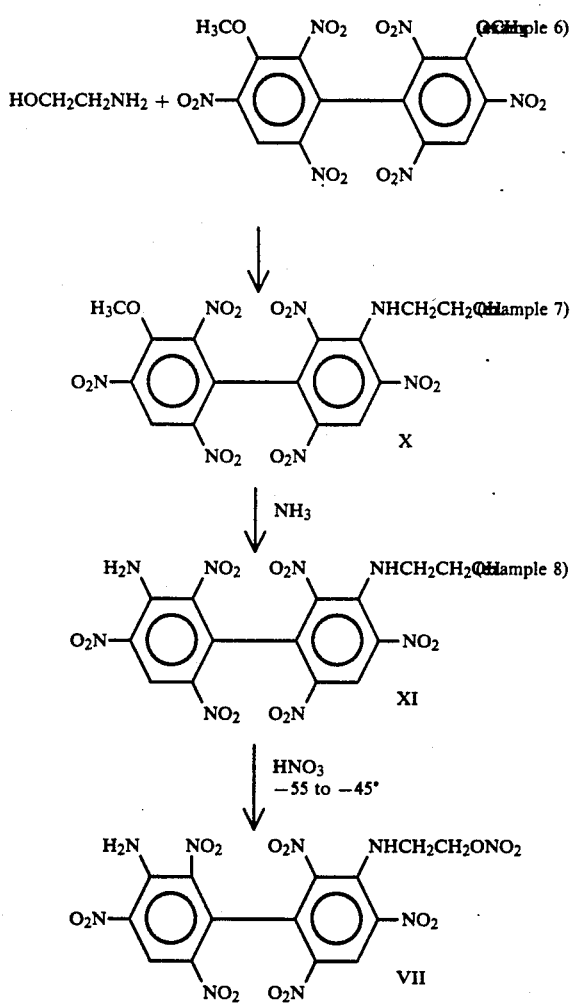

First, one mole of ethanolamine is reacted with each mole of 3,3'-dimethoxy-2,2',4,4',6,6'-hexanitrobiphenyl under the conditions given in example 6 to give 3-methoxy-3'-( 2-hydroxyethylamino)-2,2',4,4',6,6'-hexanitrobiphenyl (compound X). Compound X is then reacted with ammonia under the conditions of example 7 to produce 3-amino-3'-(2-hydroxyethylamino)-2,2',4,4',6,6'-hexanitrobiphenyl (compound XI). Compound XI is then nitrated under the conditions of example 8 to produce the product 3-amino-3'-(hydroxyethylaminonitrate)-2,2',4,4',6,6'-hexanitrobiphenyl.

The general nature of the invention having been set forth, the following examples are presented as specific illustrations thereof It will be understood that this invention is not limited to these specific examples, but is susceptible to various modifications that will be recognized by one of ordinary skill in the art.

EXAMPLE 1

1,3-Dichloro-5-(2-hydroxyethylamino)-2,4,6-trinitrobenzene (III)

Ethanolamine (1.4 g, 0.023 mole) in 15 ml of dichloroethane was added dropwise to a stirred solution of 5.1 g (0.016 mole) of 1,3,5-trichloro-2,4,6-trinitrobenzene in 50 ml of dichloroethane at room temperature. The cloudy solution (decanted from an insoluble oil) was allowed to stand overnight and a small amount (approximately 0.2 g) of insoluble solid that formed was removed by filtration. The volatiles were removed from the filtrate to give 4.6 g of sold which was digested with 25 ml of methylene chloride.

The insoluble product (1.5 g, mp 168°–172° C.) is 66% of the theoretical yield (based on 3.0 g of recovered starting material). Crystallization from dichloroethane gave the product 1,3-dichloro-5-(2-hydroxyethylamino)-2,4,6-trinitrobenzene, 1.2 g, mp 173°–175° C. An analytical sample had mp 174°–176° C.; $^1$H NMR (acetone-$d_6$+$D_2O$): 3.33 (t, 2H), 3.83 (t, 2H).

Anal Calcd for $C_8H_6N_4Cl_2O_7$: C, 28.17; H, 1.77; N, 16.43; Cl, 20.79 Found: C, 28.17; H, 1.75; N, 16.28; Cl, 20.90.

EXAMPLE 2

1,3-Diamino-5-(2-hydroxyethylamino)-2,4,6-trinitrobenzene (II)

To a mixture of 0.50 g (0.0015 mole of 1,3-dichloro-5-(2-hydroxyethylamino)-2-4,6-trinitrobenzene and methanol (10 ml) stirred in an ice bath was added a solution of gaseous ammonia in methanol until the reaction mixture remained basic to damp pH paper. The mixture was stirred at room temperature for 4 hours (kept basic with $NH_3$) and then stood overnight before the insoluble solid was removed to give the product 1,3-diamino-5-(2-hydroxyethylamino)-2,4,6-trinitrobenzene, 0.40 g (91%), mp 240° C. dec; $^1$H NMR (DMSO-$d_6$+$D_2O$): 3.14 (t, 2H), 3.70 (t, 2H).

Anal Calcd for $C_8H_{10}N_6O_7$; C, 31.79; H, 3.33; N, 27.81.

Found: C, 31.93; H, 3.24; N, 27.27.

EXAMPLE 3

1,3-Diamino-5-(hydroxyethylaminonitrate)-2,4,6 trinitrobenzene (I)

To 90% nitric acid (40 ml) stirred at −50° C. was added 2.3 g (0.0076 mole) of 1,3-dichloro-5-(2-hydroxyethylamino)-2,4,6-trinitrobenzene. The mixture was allowed to warm to −30° C. and held at this temperature until all material dissolved. The solution was poured onto ice to give 2.25 g (85%) of yellow solid the product 1,3-diamino-5-(hydroxyethylaminonitrate)-2,4,6-trinitrobenzene, mp 212° C. dec. Crystallization from acetone-methanol raised the melting point to 215° C. dec; $^1$H NMR (DMSO-d+$D_2O$): 3.48 (t, 2H), 4.95 (t, 2H).

Anal. Calcd for $C_8H_9N_7O_9$: C, 27.67; H, 2.61; N, 28.24.

Found: C, 28.18; H, 2.51; N, 27.90.

EXAMPLE 4

1-Amino-3,5-bis(2-hydroxyethylamino)-2,4,6-trinitrobenzene (VI)

Ethanolamine (0.55 g, 0.009 mole) in 8 ml of methanol was added to a solution of 0.6 g (0.002 mole) of 1-amino-3,5-dichloro-2,4,6-triniitrobenzene in 10 ml of methanol stirred at room temperature. After 2 hours the yellow precipitate was removed to give the product 1-amino-3,5-bis(2-hydroxyethylamino)-2,4,6-trinitrobenzene, 0.7 g (100%), mp 226° C. dec; $^1$H NMR (acetone-$d_6$+$D_2O$): 3.35 (t, 2H), 3.90 (t, 2H).

Anal Calcd for $C_{10}H_{14}N_6O_8$: C, 34.68; H, 4.07; N, 24.27.

Found: C, 34.72; H, 4.05, N, 24.37.

EXAMPLE 5

1-Amino-3,5-bis(hydroxyethylaminonitrate)-2,4,6-trinitrobenzene (V)

To 10 ml of 90% nitric acid stirred at −45° C. was added 0.50 g (1.44 mmole) of 1-amino-3,5-bis(2-hydroxyethylamino)-2,4,6-trinitrobenzene. The mixture was then held at −30° C. until all material dissolved. The solution was poured unto ice to give 0.61 g (97%) of a yellow solid product 1-amino-3,5-bis(hydroxyethylaminonitrate)-2,4,6-trinitrobenzene. Crystals from tetrahydrofuran-methanol had melting point 110°–112° C.; $^1$H NMR (acetone-$d_6$): 3.73 (t, 2H), 5.10 (t, 2H).

Anal Calcd for $C_{10}H_{12}N_8O_{12}$: C, 27.53; H, 2.77; N, 25.68.

Found: C, 27.75; H, 2.78; N, 25.39.

EXAMPLE 6

3-Methoxy-3'-(2-hydroxyethylamino)-2,2',4,4',6,6'-hexanitrobiphenyl (X)

Ethanolamine (0.20 g, 0.0032 mole) in 5 ml of dichloroethane was added dropwise to a stirred solution containing 2.4 g (0.005 mole) of 3,3'-dimethoxy-2,2',4,4',6,6'-hexanitrobiphenyl in 30 ml of dichloroethane. The reaction solution, after concentration to 10 ml, yielded only a small amount (0.2 g) of precipitate. The mother liquor was chromatographed on Silica gel 60 ($CH_2Cl_2$ as eluent) to give the product 3-methoxy-3'-(2-hydroxyethylamino)-2,2',4,4',6,6'-hexanitrobiphenyl, 1.2 g (70% yield, 0.8 g of starting material recovered), mp 180°–181° C.; $^1$H NMR acetone $d_6$): 3.30 (m, 2H), 3 93 (m, 2H), 4.30 (s, 3H), 9.47 (s, 1H), 9.55 (s, 1H).

EXAMPLE 7

3-Amino-3'-(2-hydroxyethylamino)-2,2',4,4',6,6'-hexanitrobiphenyl (XI)

A mixture of 0.55 g (0.0011 mole) of 3-methoxy-3'-(2-hydroxyethylamino)-2,2',4,4',6,6'-hexanitrobiphenyl and 10 ml of methanol was stirred in an ice bath while a solution of gaseous ammonia in methanol was added until the mixture remained basic to damp pH paper. The mixture was then kept basic with ammonia as it was stirred at room temperature for 3 hours. After standing overnight, the insoluble yellow solid product 3-amino-3'-(2-hydroxyethylamino)-2,2',4,4',6,6'-hexanitrobiphenyl was removed to give 0.45 g (85%), mp 246° C. dec;

$^1$H NMR (acetone-d$_6$+D$_2$O): 3.28 (t, 2H), 3.90 (t, 2H), 9.50 (overlapping s, 2H).

Anal Calcd for C$_{14}$H$_{10}$N$_8$O$_3$: C, 33.74; H, 2.02; N, 22.49.

Found: C, 33.82; H, 2.22; N, 21.83.

EXAMPLE 8

3-Amino-3'-(hydroxyethylaminonitrate)-2,2',4,4',6,6'-hexanitrobiphenyl (VII)

To 4 ml of 90% nitric acid well stirred at −55° C. was added 0.3 g (0.6 mmole) of 3-amino-3'-(2-hydroxyethylamino)-2,2',4,4',6,6'-hexanitrobiphenyl. The mixture was allowed to warm to −45° C. over 15 minutes at which time all material was in solution. The solution was poured onto ice to give 0.3 g (90%) of yellow solid which was crystallized from acetone-methanol to give the product 3-amino-3'-(hydroxyethylaminonitrate)-2,2',4,4',6,6'-hexanitrobiphenyl mp 182° C. dec; $^1$H NMR (acetone-d$_6$+D$_2$O): 3.73 (t, 2H), 5.03 (t, 2H), 9.54 (s, 1H), 9.57 (s, 1H).

Anal. Calcd for C$_{14}$H$_9$N$_9$O$_{15}$: C, 30.95; H, 1.67; N, 23.20. Found: C, 30.74; H, 1.73; N, 22.67.

EXAMPLE 9

3,3'-Bis(2-hydroxyethylamino)-2,2',4,4',6,6'-hexanitrobiphenyl (XII)

To a solution of 1.45 g (0.024 mole) of ethanolamine in 80 ml of methanol stirred in an ice bath was added 4.8 g (0.01 mole) of 3,3'-dimethoxy-2,2',4,4'6,6'-hexanitrobiphenyl. After 20 minutes at 0° C., the mixture was stirred for 4.5 hours at room temperature before the insoluble yellow solid was removed and washed with methanol. The yield of product 3,3'-bis(2-hydroxyethylamino)-2,2',4,4',6,6'-hexanitrobiphenyl was 5.15 g (95%), mp 215°-216° C. $^1$H NMR (acetone-d$_6$+D$_2$O): 3.30 (m, 4H), 3.90 (t, 4H), 9.53 (s, 2H).

EXAMPLE 10

3,3'-Bis(Hydroxyethylaminonitrate)-2,2',4,4',6,6'-hexanitobiphenyl (VIII)

To 15 ml of 90% nitric acid stirred at −45° C. was added 1.5 g (0.0028 mole) of 3,3'-bis(2-hydroxyethylamino)-2,2',4,4',6,6'-hexanitrobiphenyl. The mixture was held at −30° C. for 5 minutes until all material had dissolved. The solution was poured onto ice to give 1.7 g (96%) of yellow solid product 3,3'-bis(Hydroxyethylaminonitrate)-2,2',4,4',6,6'-hexanitrobiphenyl (essentially pure by TLC and $^1$H NMR). Crystals from acetone-methanol had mp 138°-140° C.; $^1$H NMR (acetone-d$_6$): 3.72 (m, 4H), 5.03 (t, 4H), 9.25 (broad, NH), 9.52 (s, 2H).

Anal. Calcd for C$_{16}$H$_{12}$N$_{10}$O$_{18}$: C, 30.39; H, 1.91; N, 22.15.

Found: C, 31.07; H, 2.03; N, 21.69.

EXAMPLE 11

3-(2-Hydroxyethylamino)-2,2',4,4',6,6'-hexanitrobiphenyl (XIII)

A mixture of 2.1 g (0.0046 mole) of 3-chloro-2,2',4,4',6,6'-hexanitrobiphenyl and 25 ml of methanol was stirred in an ice bath while a solution of 0.58 g (0.0095 mole) ethanolamine in 9 ml of methanol was added over 10 minutes. The mixture was stirred for 4 hours at room temperature before the insoluble material was removed and washed with a small amount of methanol to give 1.3 g of yellow solid. Removal of volatiles from the filtrate gave a dark residue which was stirred with water to give 0.8 g of dark solid. TLC and $^1$H NMR indicated the yellow solid was mainly the desired product 3-(2-hydroxyethylamino)-2,2',4,4',6,6'-hexanitrobiphenyl but also contained unreacted starting material. The dark solid contained some desired product along with dark colored impurities The yellow solid (1.3 g) was stirred with 20 ml of boiling methylene chloride before the mixture was cooled to room temperature and the insoluble yellow solid was removed to give 0.65 g, mp 190°-193° C.; $^1$H NMR (acetone-d$_6$+D$_2$O): 3.30 (t, 2H), 3.90 (t, 2H), 9.57 (overlapping s, 3H).

EXAMPLE 12

3-(Hydroxyethylaminonitrate)-2,2',4,4',6,6'-hexanitrobiphenyl (IX)

To 3 ml of 90% nitric acid stirred at −35° C. was added 0.30 g of 3-(2-hydroxyethylamino)-2,2',4,4',6,6'-hexanitrobiphenyl. The solution was held at −30° C. for 3 minutes before it was poured onto ice to give a yellow solid (0.32 g, 100%) which was essentially pure by TLC and $^1$H NMR. The solid was crystallized from acetone-methanol to give the product 3-(hydroxyethylaminonitrate)-2,2',4,4',6,6'-hexanitrobiphenyl 0.23 g, mp 162°-164° C. $^1$H NMR (acetone-d$_6$): 3.70 (t, 2H), 5.00 (t, 2H), 9.58 (overlapping s, 3H).

Anal. Calcd for C$_{14}$H$_8$N$_8$O$_{15}$: C, 31.83; H, 1.53; N, 21.21.

Found: C, 32.07; H, 1.62; N, 21.09.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. 1,3-diamino-5-(hydroxyethylaminonitrate)-2,4,6-trinitrobenzene.

2. 3-amino-3'-(hydroxyethylaminonitrate)-2,2',4,4',6,6'-hexanitrobiphenyl.

* * * * *